United States Patent [19]

Bowman et al.

[11] 4,100,220

[45] Jul. 11, 1978

[54] DIMERIZATION OF ISOBUTENE

[75] Inventors: William G. Bowman; William P. Stadig, both of Houston, Tex.

[73] Assignee: Petro-Tex Chemical Corporation, Houston, Tex.

[21] Appl. No.: 810,644

[22] Filed: Jun. 27, 1977

[51] Int. Cl.² .............................................. C07C 3/10
[52] U.S. Cl. ........................................ 260/683.15 R
[58] Field of Search ............................... 260/683.15 R

[56] References Cited

U.S. PATENT DOCUMENTS

| | | | |
|---|---|---|---|
| 2,574,325 | 11/1951 | Gislon et al. | 260/639 |
| 3,164,641 | 1/1965 | Bezzarin | 260/683.15 R |
| 3,326,866 | 6/1967 | Haag | 260/683.15 R |
| 3,370,101 | 2/1968 | Hayes et al. | 260/683.15 R |
| 3,518,323 | 6/1970 | Pine et al. | 260/683.15 R |
| 3,832,418 | 8/1974 | Bercik et al. | 260/683.15 R |
| 3,950,442 | 4/1976 | Vogel et al. | 260/641 |
| 3,994,983 | 11/1976 | Webers et al. | 260/641 |

*Primary Examiner*—C. Davis
*Attorney, Agent, or Firm*—Kenneth H. Johnson

[57] ABSTRACT

An improved process for the preparation of isobutene dimer comprising passing isobutene and a controlled amount of t-butanol and/or water (water reacts with isobutene under the conditions of the reaction to form t-butanol) through a fixed bed acidic cation exchange resin, producing only a hydrocarbon phase, removing the hydrocarbon phase, splitting the hydrocarbon phase, and recycling a portion thereof to the reaction. The recycle provides the means to control the temperature of the reaction by cooling the recycle and providing a heat sink. The controlled amount of t-butanol and/or water suppresses or inhibits the production of isobutene high polymers, e.g., trimers, tetramers and codimers (butene is also a common component of available $C_4$ feed streams).

13 Claims, 1 Drawing Figure

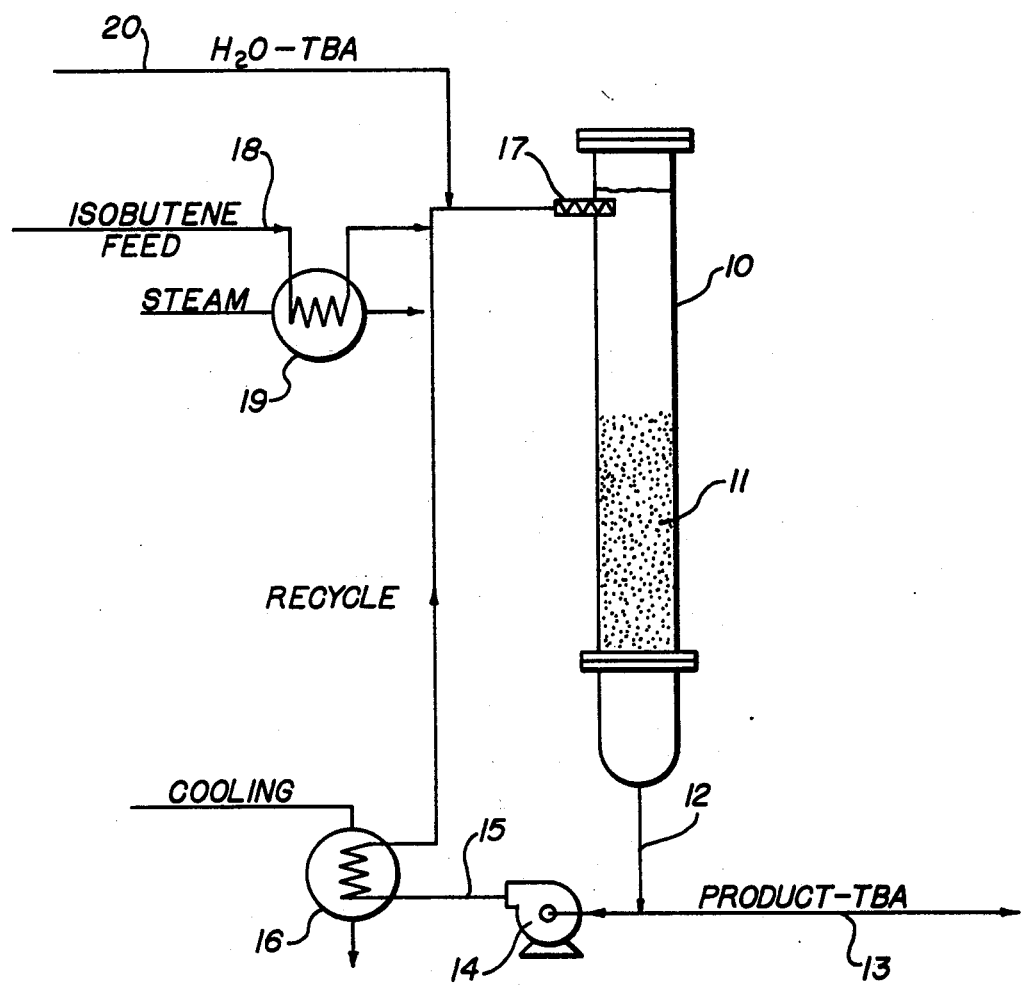

DIMERIZATION OF ISOBUTENE

BACKGROUND OF THE INVENTION

This invention relates to a process for the production of lower polymers, i.e., dimers and trimers, from isobutene. More particularly, the invention relates to a fixed bed catalytic process.

The acid catalysis of the reaction of isobutene and water to produce t-butanol is well known. More recently, acid ion exchange resins have been used as the catalysts, e.g., British patent specification Nos. 1,309,164 and 1,396,488, where the reaction of propylene and water was illustrated in a fixed bed acidic ion exchange resin with various isobutene polymers produced as by-products.

Commercial operations would have to be continuous to be feasible. Fixed bed procedures were initially proposed as the most desirable because of simplicity of operation, i.e., isobutene is passed over the catalyst and hydrocarbon phase contain polymer recovered. The reaction is exothermic and temperature control has presented a problem. However, another problem which is a serious detriment is a rapid increase in by-product formation. At the beginning of the process, the reaction proceeds as expected. Side reactions begin and increase as the reaction proceeds. The side reactions include particularly polymerization, which is uncontrolled and from which results diisobutene, triisobutene, higher oligomers, and codimers of isobutene and n-butenes.

The formation of diisobutene and triisobutene is not particularly undesirable since these materials are of commercial value. The higher oligomers, however, are substantially waste and in some cases, are dark, gummy materials, which can foul equipment or otherwise interfere with the process. Furthermore, the uncontrolled side reaction is a detriment, since product distribution cannot be adjusted as desired. It should also be noted in the prior art that by-product selectivity could be reversed only by the cessation of the reaction, back-washing of the catalyst with water or replacement of the catalyst.

As can be seen in the prior art, the dimer and/or trimer products although valuable as gasoline octane improvers were the side benefit of the t-butanol process. The maximization of lower polymers has been prevented by the presence of water which favors the hydration reaction. The prior art used large excesses of water, i.e., 3 to 35 moles of water per mole of isobutene, mainly to control the reaction temperature. In a related application by the same inventors filed of even date herewith entitled: FIXED BED PROCESS FOR THE PRODUCTION OF T-BUTANOL, Ser. No. 799,103, filed May 20, 1977 a method of isobutene hydration using a fixed bed acidic resin catalyst and less than stoichiometric amounts of water is disclosed, i.e., a mole ratio of water:isobutene of less than 0.24 to 1:1. The temperature control in the hydration process and the present polymerization process is overcome in a novel and unobvious method. In fact, the two processes are completely compatible, in a single reaction system, i.e., reactor, catalyst, feed, with the desired product being obtained by adjustment of the water content of the feed to the reactor as taught in the respective applications.

In the present invention, dimerization of isobutene is the desired result. Dimerization is understood to be the addition of one molecule of isobutene to one other molecule of isobutene to produce a product having twice the molecular weight of isobutenes. Stated otherwise, a dimerization is the reaction of olefinic molecules to produce one-half the number of other olefin molecules. The process as described below is well adapted to the production of dimer, however, some trimer (a triple isobutene molecule) and higher products are produced as well as is some codimer, resulting because most isobutene streams also contain substantial amounts of n-butene. A codimer as the term is used herein is understood to be 1 molecule of isobutene reacted with a molecule of n-butene. The dimer is easily separated from the by-products if desired.

An advantage of the present invention is a continuous commercially adaptable process for producing isobutene dimer as the principal reaction product. Another advantage is that the present process suppresses the formation of by-product polymerizations. A particular feature of this invention is the coproduction of small amounts of t-butanol and the adjustability of the process as described to allow an increase or decrease in t-butanol as desired. It is also a feature of this invention that temperature control of the fixed bed reaction has been obtained. These and other advantages will be more apparent from the further discussion of the invention.

It is an advantage of the present invention that benefits of the fixed bed isobutene dimerization and the fluidzed system are both obtained. It is a particular feature of the present invention that a method of suppressing (or controlling) higher isobutene polymerization (e.g., trimer, tetramers and copolymers) in a fixed catalyst bed has been obtained. It is also a feature of the present invention that temperature control of the fixed bed dimerization has been obtained. These and other advantages and features will be more apparent from the further discussion of the invention.

DRAWINGS

The FIGURE is a schematic representation of the dimerization process of the present invention.

SUMMARY OF THE INVENTION

Briefly stated, the present invention is a process for the preparation of isobutene dimer comprising passing isobutene and t-butanol, water or a mixture of t-butanol and water through a fixed bed of acidic cation ion exchange resin in liquid phase at a temperature in the range of 55° to 160° C, preferably above 100° C for a sufficient time to react the isobutene at a mol ratio of t-butanol to isobutene being in the range of 0.001 to 1:1 and the mol ratio of water to isobutene being less than 0.06:1 producing only a hydrocarbon phase product, recovering said hydrocarbon phase, containing t-butanol, splitting said hydrocarbon phase, cooling a portion thereof to a temperature in the range of 15° to 110° C, and recylcing the cooled hydrocarbon phase to the reaction. Isobutene dimer may be recovered from a portion of the product which is not recycled.

Generally, the isobutylene is fed as a liquid mixture of $C_4$ hydrocarbons, containing principally, saturated and monoolefinic compounds, and is fed to a fixed bed reactor containing a cation exchange resin in the hydrogen or acid form, such as Amberlyst 15. The amount of t-butanol injected in or mixed with the feed is controlled or adjusted, in accordance with the invention, such that the catalyst (resin) is maintained in a partially dehydrated condition, and there is no free water phase leaving the reactor, or the catalyst bed.

Temperatures above 100° C are preferred, because the t-butanol tends to dissociate at over 100° C and the dimerization is favored. The t-butanol may be added as such or may be produced in situ by the addition of less than 0.06 mol of water per mol of isobutene to the reaction. Since a portion of the product is recycled there may be a build up of t-butanol when water is fed. t-Butanol may be added to the feed to the reactor, such as that recovered from the split reaction product which is not recycled, although such addition may not be necessary. t-Butanol suppresses dimerization slightly, however, it is a substantial benefit in suppressing the production of trimer, higher polymers and codimers.

It is to be understood that water may be continuously or intermittently added to the feed to the reaction in the recited range even with recycle t-butanol, provided the total t-butanol in the feed to the reaction including the t-butanol equivalent represented by the reaction of any water with isobutene is within the range of 0.001 to 1 mol of t-butanol per mol of isobutene. The addition of greater amounts of water, i.e., greater than 0.06 per mol of isobutene going to the reactor in the reaction feed, tends to shift the process from a dimerization to a hydration.

DETAILED DESCRIPTION OF THE INVENTION AND PREFERRED EMBODIMENTS

A preferred process for the dimerization of isobutene comprising:
 (a) feeding a stream containing isobutene and 0.001 to 1 mol of t-butanol per mol of isobutene;
 (b) contacting said stream with a granular fixed bed acidic cation exchange resin for a sufficient time to react isobutene at a temperature of reaction in the fixed bed in the range of 55° to 160° C;
 (c) producing only a hydrocarbon phase product stream containing isobutene dimer;
 (d) splitting the product passing from said fixed bed into two portions;
 (e) recovering and removing one portion of said hydrocarbon phase product;
 (f) cooling one portion of said hydrocarbon phase product to a temperature in the range of 15° to 110° C; and
 (g) recycling said cooled hydrocarbon phase product protion to step (a).

The hydrocarbon phase portion which is recycled is preferably recycled continuously to step (a). Isobutene dimer is preferably recovered from the product of step (e).

The cooled hydrocarbon phase product which is recycled to the reaction provides the temperature control of the reaction. By adjusting the temperature of this portion, the catalyst bed temperature is maintained in the desired range. The volume ratio of recycle of hydrocarbon product: fresh isobutene feed may vary, generally in the range of from more than 0, e.g., 0.1, to 50:1, more preferably about 5 to 30:1 or up to about 20:1.

In a further embodiment of the present invention the t-butanol may be produced in situ by the intimate mixing of water in the mol ratio of less than 0.06 mol of water per mol of isobutene in the feed stream (the isobutene is based on all sources, i.e., fresh feed and recycle). Under the conditions of the dimerization the water will react with isobutene to produce t-butanol. However, as noted above, the presence of greater quantities of water will proportionally tend to shift the reaction away from isobutene dimer as the principal product towards t-butanol.

The present process is preferably carried out in a substantially vertical fixed catalyst bed; for example, a bed of cation exchange resin supported in a vertical reactor. Such reactors may range from a few inches to several feet in diameter. The depth of the bed may vary within a wide range with the reactant-catalyst contact time being adjusted by the flow of the reactants therethrough. Generally, LHSV of the isobutene 0.1 to 3.0 are employed with LHSV of 0.5 to 2.0 being preferred as based on fresh feed (i.e., excluding recycle).

The flow in the reactor may be upward or downward, with the downflow being preferred. Concurrent flow is preferred. It is believed that better reactant-catalyst contact occurs in the concurrent downward flow.

The reaction is conducted at 55° to 160° C in the reactor. There may be a temperature gradient through the bed, which preferably, is no greater than 10° to 25° C. A preferred temperature range for the reaction is 100° to 130° C. The reaction is carried out under sufficient pressure to maintain a liquid phase system, e.g., 16 to 25 atmospheres. The temperature of the feed to the reactor is adjusted to maintain the temperature in the catalyst bed as specified, which will generally mean heating the hydrocarbon feed and cooling (at least after startup) the hydrocarbon recycle. These adjustments are made for each reactor, ratio of reactant and the like, and are easily within the skill of the mechanic in the art. The heating and cooling described above may be carried on simultaneously by mixing the two streams (i.e., fresh feed and recycle).

The liquid hydrocarbon and water feed may be fed through a single line or separate lines into the reactor. Trickle or spray techniques may be used to introduce the reactants into the reactor.

The hydrocarbon phase product which is not recycled may be fractionated to recover dimer and unreacted isobutene, which may be recycled.

The isobutene reactant may comprise up to 100 percent of the hydrocarbon feed to the reactor, generally 5 to 100 percent. Frequently, the isobutene is contained in a feed stream which is substantially comprised of $C_4$ hydrocarbons, such as butene-1, butene-2 and butane. Butadiene is reactive in the process of this invention and may be desirably removed prior thereto, although amounts of 0.5 percent or less, do not present so much of a problem as to require removal.

The water (if any) is present in the reactor in an amount far less than the stoichiometric amount, that is less than 0.06 mol of water per mol of isobutene. The water is substantially free of cations. Distilled or demineralized (deionized) water may be employed. The water and isobutene may be intimately mixed by known methods to form an emulsion which is passed through the catalyst bed.

The cation resins are those which have been used in the prior art for this reaction. Catalysts suitable for the new process are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A large variety of methods may be used for preparing these polymers; for example, polymerization alone or in admixture with other monovinyl compounds, or by crosslinking with polyvinyl compounds; for example, with divinyl benzenes, divinyl toluenes, divinylphenylethers and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0 to 150° C, and the sulfuric acid should contain sufficient sulfur trioxide so that it still contains 10 to 50% free sulfur trioxide after the reaction. The resulting products preferably contain an average of 1.3 to 1.8 sulfonic acid groups per aromatic nucleus. Particularly, suitable polymers which contain sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, German Pat. No. 908,247).

The ion exchange resin is preferably used in a granular size of about 0.15 to 1 mm, although particles of 250$\mu$ up to about 1 mm may be employed. The finer catalysts provide high surface area, but also result in high pressure drops through the reactor.

The following examples are illustrative of the invention (or prior art) and are not intended to be determinative of the scope of the invention.

Referring now to the drawing, one mode of operation will be described. The reactor 10 is a vertical stainless steel tubular reactor with the resin catalyst bed 11 supported through the middle portion. The hydrocarbon phase product (the only product phase) is removed via line 12. The stream 12 is split and a portion 13 is sent for storage or processing to recover isobutene dimer and unreacted isobutene for recycle (not shown) to line 18 which is the isobutene feed. A portion of the hydrocarbon phase product from line 12 passes via 15 for recycle to mix with incoming isobutene feed 18. This stream 15 contains dimer, unreacted isobutene and some t-butanol (also other by-products).

The isobutene feed 18 passes through a heat exchange 19 where its temperature is adjusted usually by heating and hence, into the recycle line 15. (Note the heating of feed 18 and cooling of recycle 15 may be carried out as the same step by direct or indirect contacting of the two). Reaction water if any is added via 20 to the combined streams 18 and 15. The three streams (fresh feed, recycle and water) pass through static mixer 17 into the reactor 10 and down through the resin bed 11. Since there is not an excess of water, only a hydrocarbon phase passes from the bed. The recycle stream is pumped by pump 14 into recycle line 15 which passes through heat exchanger 16 where it is cooled (note above). On startup, the heat exchanger 16 may be used to heat the recycle. Other items of standard equipment are not shown, but would be employed as obviously desirable or necessary, e.g., safety valves, liquid level indicators, drains, vents, etc.

EXAMPLE 1

This example demonstrates a typical prior art process without recycle. The runs were made in a 1 inch ID reactor. The conditions of the process, feed and results are all set forth in Table I.

TABLE I

Reactor 1" × 24"; Resin 200 mls.(wet); *Amberlyst 15; Temperature 98° - 100° C; Pressure, 220 psig; Hydrocarbon, LHSV 1.07; $H_2O$, LHSV 0.42; $H_2O/iC_4$ = Molar Ratio 4.3

| Hours on Stream | | 3.5 | 4.8 | 7.0 | 8.0 |
|---|---|---|---|---|---|
| Gas Analysis**(Mole %) | Feed | \multicolumn{4}{c}{Raffinate} | | | |
| $iC_4$ | 2.8 | 5.2 | 3.8 | 4.1 | 5.4 |
| $nC_4$ | 6.0 | 8.1 | 8.6 | 8.9 | 8.1 |
| $C_4^=1$ | 24.5 | 36.4 | 35.0 | 35.4 | 36.7 |
| $iC_4^=$ | 48.0 | 27.3 | 25.5 | 23.1 | 26.4 |
| Low boiling $C_4^=2$ | 10.9 | 13.5 | 16.0 | 16.6 | 13.8 |
| High boiling $C_4^=2$ | 4.3 | 4.9 | 6.5 | 7.0 | 5.0 |
| $C_4H_6$ | 3.5 | 4.7 | 4.5 | 5.0 | 4.7 |
| Isobutylene Conversion | | 59.3 | 62.9 | 67.5 | 61.1 |
| Selectivity | | | | | |
| t-BuOH | | 97.6 | 88.9 | 78.3 | 75.9 |
| Dimer | | 2.39 | 11.0 | 20.7 | 23.3 |
| Trimer | | trace | 0.1 | 1.0 | 0.85 |
| Butadiene Conversion | | 5.8 | 10.3 | 4.6 | 6.4 |

*Cation exchange resin, highly crosslinked, macroreticular, sulfonated, 45m² surface area, 32% porosity, 1.8 meq/ml (2.9 meq/g) exchange capacity. (Rohm and Haas Co.)
**Analytical data for water-TBA is provided by GC using a 4' × ⅛" Porapak QS column at 220° C thermal conductivity detection; for TBA-isobutene dimer, trimer and heavy polymers a 41' × ⅛" DC710 on Teflon column at 220° C with flame ionization detection is used. Appropriate sensitivity factors are used for both columns.

EXAMPLES 2–32

These examples illustrate the invention, and in addition illustrate a t-butanol process as discussed above. Comparison of these results, as shown in Table II, with the standard, prior art type of process shown in Example 1, shows very good conversions and selectivities. The reactor was a 12-inch I.D. stainless steel pipe, containing 8.4 cubic feet of Amberlyst 15* resin. The conditions and process variables of each run are specified in Table II.

*Rohn and Haas Company, Philadelphia, Pa, Sulfonated polystyrene (divinyl benzene crosslinked); resin beads, (20–50 mesh) having macroreticular structure, cation exchange characterized as strong acid, active group —$SO_3$—H+.

TABLE II

| Example | Fresh Hcbn. Feed[1] LHSV | Hcbn. Recirc Rate gpm | $H_2O$ Injection Rate, lbs/min[6] | Molar Ratio $H_2O/iC_4^=$ Based on Feed Only | Based on Feed + Recycle | Temp. °F Inlet | Max | Conv.[5] Mol % | TBA | $iC_4^=$ Sel. Mol % Dimer and[3] Codimer | $C_9+$ | Conv.[5] Mol % | $C_4^=$ Sel. Mol % trans $C_4^=2$ | cis $C_4^=2$ | Sec-butyl Alcohol | Analysis of Dimer Product[4] Dimer | Weight % Dimer 2 | Codimer | $C_9+$ |
|---|---|---|---|---|---|---|---|---|---|---|---|---|---|---|---|---|---|---|---|
| 2 | 0.935 | 3.9 | 0.26 | 0.33 | 0.12 | 200 | 221 | 49.3 | 52.9 | 44.4 | 2.72 | — | — | — | — | | | | |
| 3 | 1.03 | 3.68 | 0.38 | 0.44 | 0.17 | 204 | 220 | 46.6 | 67.2 | 30.9 | 2.0 | 8.3 | 5.6 | — | 54.6 | | | | |
| 4 | 1.03 | 3.68 | 0.38 | 0.44 | 0.17 | 205 | 220 | 45.1 | 71.5 | 27.2 | 1.4 | 8.4 | 20.1 | — | 39.9 | | | | |
| 5 | 1.03 | 3.68 | 0.38 | 0.44 | 0.17 | 206 | 220 | 44.5 | 74.5 | 24.4 | 1.05 | 6.0 | 39.3 | 11.8 | 60.7 | | | | |
| 6 | 0.992 | 3.68 | 0.19 | 0.23 | 0.067 | 217 | 228 | 41.5 | 56.4 | 41.7 | 1.8 | 10.3 | 8.6 | 1.45 | 57.3 | | | | |
| 7 | 1.05 | 5.03 | 0.19 | 0.24 | 0.070 | 224 | 246 | 45.2 | 46.8 | 51.0 | 2.2 | 18.8 | 1.5 | 22.2 | 41.7 | | | | |
| 8 | 1.03 | 5.03 | 0.22 | 0.25 | 0.066 | 226 | 240 | 46.4 | 43.5 | 53.8 | 2.7 | 19.8 | 10.3 | 24.3 | 40.1 | | | | |
| 9 | 1.03 | 5.03 | 0.22 | 0.25 | 0.073 | 228 | 243 | 51.6 | 40.8 | 56.4 | 2.8 | 24.19 | | 28.5 | | | | | |
| 10 | 0.99 | 4.3 | 0.19 | 0.23 | 0.065 | 227 | 244 | 54.1 | 33.4 | 62.0 | 4.6 | 23.9 | | | | 66.1 | 23.6 | 6.2 | 3.9 |
| 11 | 0.99 | 4.3 | 0.25 | 0.30 | 0.101 | 221 | 240 | 51.4 | 39.3 | 56.7 | 4.0 | 35.7 | | | | 63.8 | 23.4 | 6.5 | 6.3 |
| 12 | 0.99 | 4.5 | 0.25 | 0.30 | 0.097 | 218 | 239 | 50.0 | 42.4 | 55.1 | 2.5 | | | | | 64.0 | 23.2 | 7.2 | 5.6 |
| 13 | 0.84 | 4.6 | 0.19 | 0.27 | 0.078 | 217 | 238 | 51.4 | 41.3 | 55.6 | 2.6 | | | | | 64.4 | 23.8 | 7.3 | 4.5 |
| 14 | 0.84 | 4.6 | 0.19 | 0.27 | 0.080 | 221 | 240 | 51.7 | 41.5 | 55.9 | 2.8 | | | | | 65.3 | 23.8 | 7.2 | 3.7 |
| 15 | 0.84 | 4.58 | 0.19 | 0.27 | 0.080 | 220 | 243 | 59.4 | 41.5 | 55.3 | 3.2 | 27.0 | 2.9 | 31.2 | 19.6 | 62.3 | 25.5 | 7.6 | 4.6 |
| 16 | 0.84 | 4.45 | 0.10 | 0.15 | 0.060 | 224 | 259 | 67.9 | 23.4 | 69.3 | 7.3 | 41.5 | 23.2 | 33.9 | 29.0 | 63.7 | 23.1 | 7.9 | 6.3 |
| 17 | 0.81 | 4.45 | 0.10 | 0.15 | 0.060 | 217 | 251 | 63.9 | 24.6 | 68.0 | 7.3 | 35.2 | 18.9 | 37.9 | 12.8 | 61.9 | 23.3 | 7.4 | 7.4 |
| 18 | 0.668 | 4.52 | 0.10 | 0.18 | 0.060 | 224 | 249 | 65.6 | 25.0 | 67.2 | 7.8 | 39.4 | 20.4 | 34.4 | 33.0 | 61.9 | 22.5 | 7.3 | 8.4 |
| 19 | 0.687 | 4.58 | 0.09 | 0.16 | 0.050 | 219 | 248 | 66.1 | 23.6 | 68.1 | 8.3 | 39.2 | 20.5 | 30.9 | 31.1 | 61.4 | 22.9 | 7.4 | 8.3 |
| 20 | 0.865 | 6.7 | 0.06 | 0.08 | 0.036 | 219 | 253 | 74.7 | 12.3 | 73.2 | 14.5 | 46.6 | 36.5 | 37.6 | 24.5 | 58.0 | 25.9 | 7.9 | 8.2 |
| 21 | 0.847 | 7.3 | 0.06 | 0.08 | 0.040 | 222 | 248 | 72.7 | 13.4 | 71.9 | 14.7 | 50.8 | 26.8 | 36.9 | 25.2 | 59.7 | 22.1 | 7.1 | 11.1 |
| 22 | 0.847 | 7.3 | 0.06 | 0.08 | 0.038 | 219 | 243 | 73.7 | 15.4 | 71.1 | 13.5 | 44.7 | 16.7 | 31.7 | 25.4 | 60.0 | 21.5 | 7.5 | 11.0 |
| 23 | 0.82 | 4.8 | 0.31 | 0.45 | 0.12 | 201 | 222 | 49.9 | 77.9 | 21.8 | 0.3 | 12.9 | 0.0 | 19.1 | 31.1 | 59.9 | 22.7 | 7.9 | 9.5 |
| 24 | 0.82 | 4.7 | 0.41 | 0.60 | 0.17 | 199 | 215 | 54.7 | 83.2 | 16.5 | 0.3 | 7.4 | 0.0 | 52.0 | 34.4 | | | | |
| 25 | 0.84 | 4.8 | 0.31 | 0.44 | 0.18 | 209 | 222 | 57.5 | 96.2 | 3.7 | 0.1 | 2.1 | | | 100 | | | | |
| 26 | 0.84 | 4.8 | 0.31 | 0.44 | 0.17 | 202 | 223 | 56.9 | 95.3 | 4.5 | 0.2 | 2.2 | | | 100 | | | | |
| 27 | 0.82 | 5.8 | 0.27 | 0.39 | 0.15 | 219 | 229 | 56.4 | 94.3 | 5.5 | 0.3 | 2.8 | | | 100 | | | | |
| 28 | 0.84 | 5.8 | 0.23 | 0.33 | 0.13 | 219 | 237 | 54.4 | 92.1 | 6.3 | 1.6 | 4.1 | 4.4 | 13.1 | 73.9 | | | | |
| 29 | 0.60 | 3.42 | 0.31 | 0.61 | 0.19 | 211 | 226 | 54.6 | 93.2 | 6.6 | 0.3 | 2.4 | | | 100 | | | | |
| 30 | 1.09 | 6.97 | 0.41 | 0.45 | 0.13 | 211 | 224 | 52.4 | 93.1 | 6.5 | 0.4 | 7.6 | | | 40.7 | | | | |
| 31 | 0.57 | 7.10 | 0.046 | 0.10 | 0.037 | 215 | 239 | 81.4 | 10.2 | 71.4 | 18.3 | 51.5 | 31.2 | 31.4 | 18.4 | 55.5 | 20.5 | 8.1 | 15.9 |
| 32[2] | 0.84 | 7.3 | 0.13 | 0.16 | 0.04 | 178 | 201 | 58.8 | 26.3 | 70.7 | 3.1 | 22.4 | 39.0 | 50.3 | 10.7 | 57.5 | 20.3 | 8.0 | 14.2 |

*[1]$iC_4^=$ in feed was ~50% (±1.5%) unless specified otherwise. The feed varied over the weeks of the evaluations set out above, the conversions are based on the actual weight % of isobutene (t-butanol) or n-butene (secondary alcohol product) in the feed. A typical feed analysis, e.g., Example 23 is iso-$C_4$-2.79%; n-$C_4$-8.15%; n-$C_4^=$-1·24.60%; iso-$C_4^=$-51.19%; trans n-$C_4^=2$-11.12%; cis n-$C_4^=2$-2.16%.
*[2]iso-$C_4$-2.65%; n-$C_4$-7.55%; n-$C_4^=$-1-19.40%; iso-$C_4^=$-59.97%; trans n-$C_4^=2$-8.49%; cis n-$C_4^=2$-1.94%. The pressure in the reactor was usually ~300 psi (5 or −10), except Example 32 where it was 285 psi.
*[3]This analysis was carried out, using GC on samples containing TBA.
*[4]The dimer analysis was carried out using GC on ample from which TBA had been removed by water washing and is considered more accurate. $C_9+$ indicates polymers higher than dimer.
*[5]Conversion is based on fresh hydrocarbon feed (stream 18) and product (stream 12).
*[6]Calculated.

The invention claimed is:

1. A process for the preparation of isobutene dimer comprising passing isobutene and t-butanol, water or a mixture of t-butanol and water through a fixed bed of acidic cation exchange resin catalyst in liquid phase at a temperature in the range of 55° to 160° C for a sufficient time to react isobutene, the mol ratio of t-butanol to isobutene being in the range of 0.001 to 1.0:1 and the mol ratio of water to isobutene being less than 0.06: provided that the total amount of t-butanol including the equivalent represented by the reaction of water present with isobutene is within the mol ratio of t-butanol to isobutene range of 0.001 to 1.0:1, producing only a hydrocarbon phase, recovering said hydrocarbon phase, containing isobutene dimer, splitting said hydrocarbon phase, cooling one portion thereof to a temperature in the range of 15° to 110° C and recycling the cooled portion to the reaction.

2. A process for the preparation of isobutene dimer comprising:
   (a) feeding a stream containing isobutene and 0.001 to 1 mol of t-butanol per mol of isobutene;
   (b) contacting said stream with a granular fixed bed acidic cation exchange resin for a sufficient time to react isobutene at a temperature of reaction in the fixed bed in the range of 55° to 160° C;
   (c) producing only a hydrocarbon phase product stream containing isobutene dimer;
   (d) splitting the hydrocarbon phase product passing from said fixed bed into two portions;
   (e) recovering and removing one portion of said hydrocarbon phase product;
   (f) cooling one portion of said hydrocarbon phase product to a temperature in the range of 15° to 110° C; and,
   (g) recycling said cooled hydrocarbon phase product portion to step (a).

3. The process according to claim 2 wherein the temperature in the reaction in the fixed bed is over 100° C.

4. The process according to claim 3 wherein the temperature gradient in the fixed bed is no greater than 25° C.

5. The process according to claim 2 wherein the acidic cation exchange resin contains sulfonic acid groups.

6. The process according to claim 2 wherein the resin has a granular size of about 0.15 to 1 mm.

7. The process according to claim 2 wherein said cooled hydrocarbon phase product portion is continuously recycled to step (a).

8. The process according to claim 2 wherein said isobutene is a component of a stream substantially comprising $C_4$ hydrocarbons.

9. The process according to claim 8 wherein said isobutene comprises 5 to 100 percent of said $C_4$ hydrocarbons.

10. The process according to claim 2 wherein said fixed bed is positioned in a vertical reactor.

11. The process according to claim 2 wherein the recycle hydrocarbon phase of step (g) is returned to step (a), in a volume ratio of 0.1 to 50:1, recycle:isobutene of step (a).

12. The process according to claim 2 wherein isobutene dimer is recovered from the hydrocarbon phase product of step (e).

13. The process according to claim 2 wherein up to 0.06 mol of water per mol of isobutene is added to said stream of step (a).

* * * * *